US005885621A

United States Patent [19]
Head et al.

[11] Patent Number: 5,885,621
[45] Date of Patent: Mar. 23, 1999

[54] TREATMENT OF A HEMOGLOBINOPATHY

[75] Inventors: C. Alvin Head, Winchester; Warren M. Zapol, Concord, both of Mass.

[73] Assignee: The General Hospital Corporation, Boston, Mass.

[21] Appl. No.: 832,913

[22] Filed: Apr. 4, 1997

Related U.S. Application Data

[60] Provisional application No. 60/014,886 Apr. 5, 1996.
[51] Int. Cl.$^6$ .......................... A61K 31/165; A61K 33/00
[52] U.S. Cl. ......................... 424/718; 514/624; 514/815
[58] Field of Search .................................. 514/634, 815, 514/624; 424/718

[56] References Cited

U.S. PATENT DOCUMENTS

| 4,954,526 | 9/1990 | Keefer ..................................... | 514/611 |
| 5,155,137 | 10/1992 | Keefer et al. ........................... | 514/611 |
| 5,380,945 | 1/1995 | Murad et al. ........................... | 564/108 |

FOREIGN PATENT DOCUMENTS

WO 92/10228   6/1992   WIPO .

OTHER PUBLICATIONS

C.D.R. Borland et al., A Comparison Of The Rate Of Reaction Of Nitric Oxide (No) With Human Whole Blood And Plasma: Gaseous No Reacts More Rapidly With Red Cells Than Plasma, p. A792, (1989).
BT Catalyst, Duke Research Piques Apex's Interest; May Yield Collaboration, May 1996, Biotechnology Center vol. 10, No. 4, pp. 1–2.
Gustave Freeman, M.D. et al., Identification Of Nitric Oxide (NO) In Human Blood, Jan./Feb. 1978, Archives of Environmental Health, pp. 19–23.
Barbara S. Shapiro et al., The Acute Painful Episode, (1994) Sickle Cell Disease: Basic Principles and Clinical Practice, 35:531–543.
J.M. Salhany et al., Correlation between Quaternary Structure and Ligand Dissociation Kinetics for Fully Liganded Hemoglobin, (1975) Biochemistry, vol. 14, No. 10, pp. 2180–2190.
Calogero Messana et al., Influence of Quaternary Structure of the Globin on Thermal Spin Equilibria in Different Methemoglobin Derivatives, (1978) Biochemistry, vol. 17, No. 17, pp. 3652–3662.
Robert C. Darling et al., The Effect of Methemoglobin on the Equilibrium Between Oxygen and Hemoglobin, (1942) The American Journal of Physiology, vol. 137 pp. 56–68.
Helen R. Sunshine et al., Requirements for therapeutic inhibition of sickle haemoglobin gelation, Sep. 21, 1978, Nature, vol. 275 pp. 238–240.
Walter S. Root, Carbon Monoxide, Handbook of Physiology—Respiration II, 43:1087–1098, (1943).
F.J.W. Roughton et al., The Effect of Carbon Monoxide on the Oxyhemoglobin Dissociation Curve, Oct. 29, 1943 from the Fatigue Laboratory, Harvard University, Boston, Mass, pp. 17–31.

Li Jia, et al., S–nitrosohaemoglobin: a dynamic activity of blood involved in vascular control, Mar. 21, 1996, Nature, vol. 380, pp. 221–226.
Sandra Blakeslee, Study Finds Major New Task Of Hemoglobin in the Blood, Mar. 21, 1996, The New York Times continued on p. A22, col. 3.
Mark A. Goldberg, M.D., et al., Treatment of Sickle Cell Anemia with Hydroxyurea and Erythropoietin, Aug. 9, 1990, New England Journal of Medicine, 323:336–372.
Samuel Charache, M.D., et al., Effect of Hydroxyurea on the Frequency of Painful Crises in Sickle Cell Anemia May 18, 1995, New England Journal of Medicine, vol. 332 No. 20, pp. 1317–1322.
Thomas R. Kinney et al., Compound Heterozygous States, (1994) Sickle Cell Disease: Basic Principles and Clinical Practice, 29:437–451.
Louis Ignarro et al., Nitric Oxide, Biochemistry, Molecular Biology, and Therapeutic Implications, (1995) Advances in Pharmacology, vol. 34, p. 387.
Teddy G. Traylor et al., Why No?, Mar. 24, 1992, Biochemistry, vol. 31, No. 11, pp. 2847–2849.
Robert C. Griggs, M.D. et al., The Biophysics of the Variants of Sickle–Cell Disease, Sep. 30, 1955 A.M.A. Archives of Internal Medicine, pp., 315–326.
Robin W. Briehl et al., Gelation of Sickle Cell Haemoglobin, II Methaemoglobin, (1974) J. Mol. Biol. 89:759–766.
L. Jia, et al., No hypertension?, Mar. 21, 1996, Nature, 1 page.
Eraldo Antonini et al., Preparation and Kinetic Properties of Intermediates in the Reaction of Hemoglobin and Ligands, Mar. 15, 1996, Squalene Biosynthesis, vol. 241, No. 13, pp. 3236–3238.
Edwin G. Moore et al., Cooperativity in the Dissociation of Nitric Oxide from Hemolobin, May 10, 1976 The Journal of Biological Chemistry, vol. 251, No. 9, pp. 2788–2794.
Q.H. Gibson, The Kinetics and Equilibria of the Reactions of Nitric Oxide with Sheep Haemoglobin, (1957) 136:507–526.
Michael P. Doyle et al., Oxidation of Nitrogen Oxides by Bound Dioxygen in Hemoproteins, (1981) Journal of Inorganic Biochemistry 14:351–358.
C. Toothill, The Chemistry of the In Vivo Reaction Between Haemoglobin and Various Oxides of Nitrogen, (1967) Brit. F. Anaesth., 39:405–412.
Robin W. Briehl et al., Gelation of Sickle Hemoglobin, III. Nitrosyl Hemoglobin, (1975) J. Mol. Biol. 96:733–743.

(List continued on next page.)

Primary Examiner—Theodore J. Criares
Attorney, Agent, or Firm—Fish & Richardson, P.C.

[57] ABSTRACT

Disclosed are methods for treating a patient identified as having a hemoglobinopathy that is characterized by a reduced affinity of hemoglobin for oxygen. The methods involve providing gaseous nitric oxide and/or carbon monoxide for (i) inhalation by the patient or (ii) ex vivo treatment of the patient's erythrocytes. Alternatively, a nitric-oxide-releasing compound can be administered to the patient.

52 Claims, 8 Drawing Sheets

OTHER PUBLICATIONS

Benjamin Gaston et al., Endogenous nitrogen oxides and bronchodilator S–nitrosothiols in human airways, Dec. 1993, Proc. Natl. Acad. Sci. USA, vol. 90, No. 23, pp. 10957–10961.

Hajime Oda, M.D. et al., Nitrosyl–Hemoglobin Formation in the Blood of Animals Exposed to Nitric Oxide Sep. 1975, Arch. Eviron. Health, vol. 30, pp. 453–456.

Mitsuaki Moriguchi et al., Nitric Oxide Can Modify Amino Acid Residues in Proteins, Mar. 16, 1992 Biochemical and Biophysical Research Communications, vol. 183, No. 2, pp. 598–604.

Kazunori Kon et al., Effect of Nitric Oxide on the Oxygen Transport of Human Erythrocytes, (1977) Journal of Toxicology and Environmental Health, 2:1109–1113.

Vijay S. Sharma et al., Reaction of Nitric Oxide with Heme Proteins and Model Compounds of Hemoglobin, (1987) Biochemistry, 26:3837–3843.

Ernest Beutler et al., The Effect of Methemoglobin Formation in Sickle Cell Disease, (1961), J. Clin. Invest. 40:1856–1871.

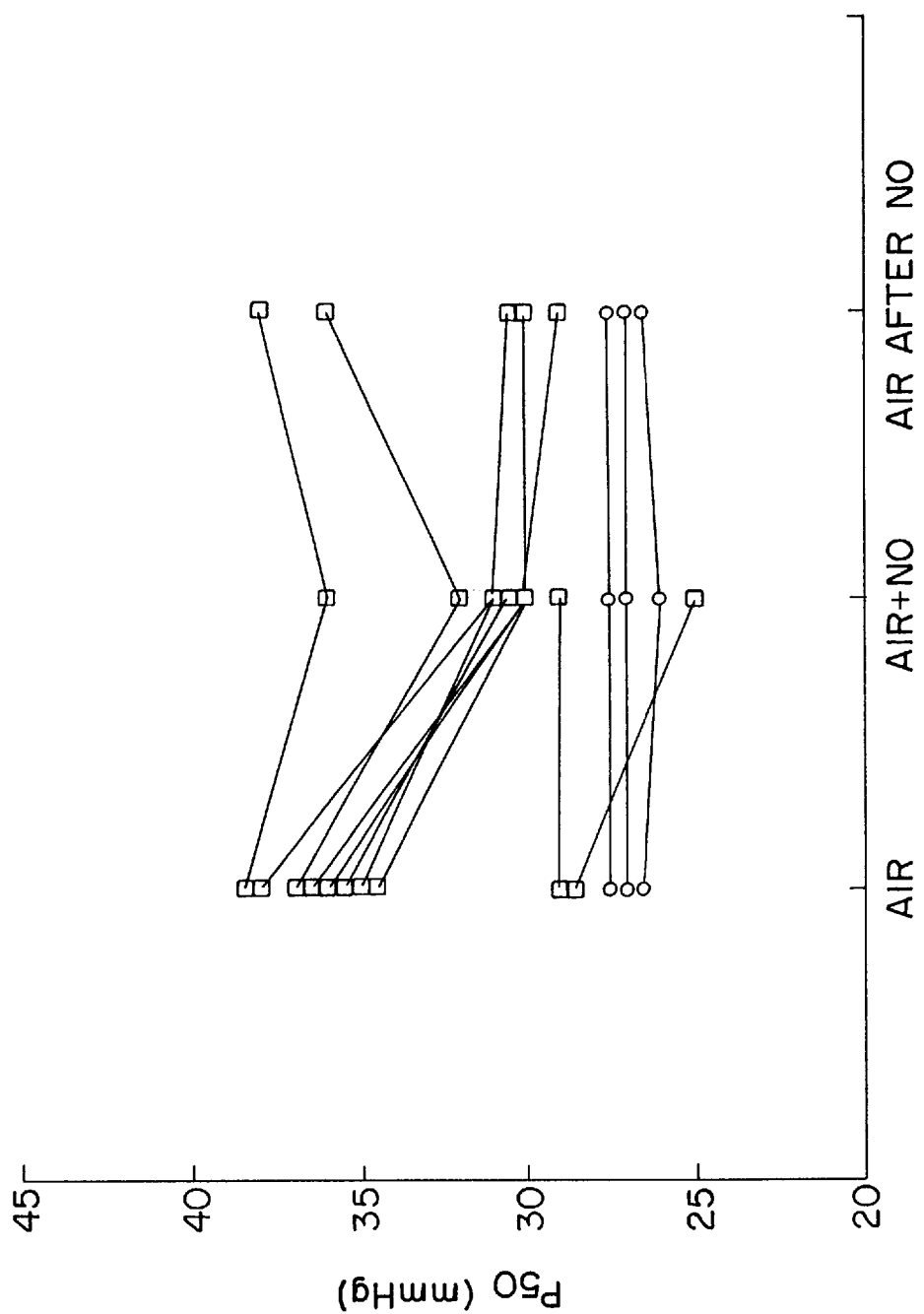

TREATMENT OF A HEMOGLOBINOPATHY

CROSS-REFERENCE TO RELATED APPLICATION

This application claims priority under 35 U.S.C. § 119 from U.S. Ser. No. 60/014,886, filed Apr. 5, 1996.

STATEMENT AS TO FEDERALLY SPONSORED RESEARCH

This invention was made at least in part with funds from the federal government under USPHS grant NHLBI-HL 42397, awarded by the National Institutes of Health. The government therefore has certain rights in the invention.

BACKGROUND OF THE INVENTION

The field of the invention is hemoglobinopathies.

A number of hemoglobinopathies are associated with a decreased affinity of oxygen for hemoglobin (Hb). Examples of such hemoglobinopathies include sickle cell disease (SCD) and sickle cell trait; the thalassemias; Hb-C, Hb-D, Hb-E, Hb-H, Hb-I, Hb-O-Arab, and Hb-Kansas disorders; and mixed heterozygous combinations of any of these. Perhaps the most extensively studied hemoglobinopathy is sickle cell disease (SCD), which results from a mutation at the sixth amino acid from the N-terminus of the β-polypeptide chain of hemoglobin (Hb-S). This mutation replaces the negatively charged amino acid glutamate (encoded by GAG) with a neutral, hydrophobic residue, valine (encoded by GUG). At physiologically relevant concentrations (e.g., about 0.2 g/cm$^3$), and under certain conditions such as hypoxia, Hb-S molecules aggregate into multi-stranded polymers, forming a viscous or solid-like gel. This polymerization of Hb-S within red blood cells (erythrocytes) distorts the erythrocytes into a variety of abnormal shapes, some of which resemble sickles. Polymerization of Hb-S also causes erythrocytes to become more rigid, decreasing the cells ability to traverse the narrow vessels of the microvasculature.

Individuals who carry one gene encoding normal adult hemoglobin (Hb-A) and one encoding Hb-S are said to have sickle cell trait. Such heterozygotes rarely suffer clinical symptoms, but can of course pass the mutant gene on to their offspring. Individuals who are homozygous for Hb-S or a combination of Hb-S and Hb-C are said to have sickle cell disease (SCD); these individuals are referred to herein as "SS." Adults whose RBCs contain normal hemoglobin are referred to herein as "AA."

Clinically, SCD is associated with chronic hemolysis, which can lead to anemia and jaundice. SCD is also associated with acute episodic vaso-occlusive crises, known as sickle crises. During such a crisis, the microvasculature can become transiently or permanently occluded, and nearly every organ of the body can be damaged as a result of the decreased oxygen supply. Such organ damage is the major cause of the mortality and morbidity associated with SCD. Infarction (i.e., necrosis of tissue due to insufficient blood supply) of bone, spleen, kidney, and lungs is particularly common, and results in severe pain that can last for several days.

Conventional methods for treating hemoglobinopathies such as SCD include performing blood transfusions on anemic patients to produce a hemoglobin level of 10 g/dl and/or achieve a total hematocrit concentration of 30%. Other methods involve using hydroxyurea to reduce erythrocyte sickling by increasing the level of fetal hemoglobin (Hb-F) in erythrocytes (Charache et al., 1995, N. Eng. J. Med. 332:1317–1322; Goldberg et al., 1990, N. Eng. J. Med. 323:366–372). Using this method, several weeks of treatment are needed to increase the level of Hb-F; this method, therefore, is not particularly useful for responding to a sickle crisis. Additional treatment methods include providing supportive therapies, such as oxygen therapy, analgesics, and hydration. Such supportive therapy is provided to the patient until the crisis is resolved, which usually takes several days.

For any given hemoglobinopathy, the affinity of the patient's hemoglobin for oxygen can be measured by generating an oxyhemoglobin dissociation curve (ODC) characteristic of the patient's total hemoglobin. This mathematical curve can be generated by plotting the percent oxygen saturation ($S_aO_2$) of the total hemoglobin on the y axis versus the partial pressure of oxygen ($P_aO_2$) in mm Hg over a wide range of oxygen pressures (e.g., 0 to 100 mm Hg) on the x axis (see, e.g., Bunn and Forget, *Hemoglobin: Molecular Genetics and Clinical Aspects*, 1986, W. B. Saunder, Publisher). The $P_aO_2$ at which half-maximal oxygen saturation of total hemoglobin occurs is termed the $P_{50}$ value. Hemoglobin that has a decreased ability to bind oxygen is characterized by a rightward shift in the ODC, relative to the ODC obtained with normal adult hemoglobin (Hb-A); this can alternatively be expressed as an increase in $P_{50}$, compared to Hb-A. Normal hemoglobin at 37°, $PaCO_2$ 40 mm Hg, pH 7.40, and isotonic conditions has a $P_{50}$ of approximately 26 mm Hg, while Hb-S has a $P_{50}$ of approximately 37 mm Hg. The $P_{50}$ value of a given patient's hemoglobin can be measured readily by commercially available equipment, such as the HEMOX-ANALYZER™ automatic blood oxygen dissociation analyzer (TCS Medical Products Company, Huntingdon Valley, Pa.).

SUMMARY OF THE INVENTION

It has now been found that nitric oxide (NO) and/or carbon monoxide (CO), or an NO-releasing compound, can be used at non-toxic levels to treat a patient identified as having any of a particular class of hemoglobinopathies. These hemoglobinopathies, which include not only SCD and sickle cell trait, but also Hb-C, Hb-D, Hb-E, Hb-H, Hb-I, and Hb-Kansas disorders, and combinations of these or other β-globin mutants (e.g., the β-thalassemias) with Hb-S, are characterized by a reduced affinity of the patient's hemoglobin for oxygen, compared with the affinity for oxygen displayed by normal adult hemoglobin (Hb-A). The method involves providing a therapeutic gas for inhalation by the patient, where the therapeutic gas includes a therapeutically effective amount of gaseous NO. In a variation of this method, the patient is treated with a therapeutic gas that includes a therapeutically effective amount of gaseous CO, or a combination of NO and CO. The treatment of the invention increases the affinity of the patient's hemoglobin for oxygen, making it function more like Hb-A. This can be quantified, if desired, by measuring the $P_{50}$ or the ODC of the patient's hemoglobin (either as cell-free hemoglobin or in intact erythrocytes) both before and after the treatment is administered. If the patient's hemoglobinopathy is SCD, the methods of the invention have the further significant benefit of decreasing the tendency of the patient's Hb-S to polymerize, and therefore the likelihood the patient's erythrocytes will sickle. Without being bound to any particular theory, it is noted that one possible mechanism by which NO therapy may work could be by affecting RBC membranes or membrane channels.

Preferably, the therapeutic gas is provided in the absence of tobacco smoke and includes NO at a concentration of at least 1 part per million (ppm) in an inert gas such as nitrogen ($N_2$) or helium (He), in air, in air supplemented with additional oxygen ($O_2$), or in another $O_2$-containing gas (e.g., an $O_2/N_2$ mixture containing from 20% up to about 99% oxygen). The concentration of NO or CO in the therapeutic gas would in general be expected to be at least 10 ppm, and preferably at least 20 or 40 ppm. Depending on the length of time the gas is inhaled in a given treatment session, useful concentrations of the NO or CO would range from 1 to 10,000 ppm (e.g., 20 to 4000 ppm or 40 to 2000 ppm). It is expected that a patient could receive a therapeutic benefit from continuously or intermittently inhaling 20, 40, 80, 100, 160, or 200 ppm NO or CO for long periods of time. Where CO is used, the dose should be controlled so that in general the patient's carboxy-Hb does not exceed 20% of total Hb. Alternatively, the NO or CO could be provided at a relatively high concentration such as 300, 400, 500, 1000, 1500, or even 2000 ppm, particularly where the patient inhales the therapeutic gas for only a brief period of time before switching back to air or oxygen. When the therapeutic gas includes CO, a useful benchmark would be to use a concentration of CO that produces 2 to 10% carboxy-Hb in the patient's blood, as measured by conventional means. The therapeutic gas provided for inhalation would preferably also include oxygen (e.g., approximately 20% oxygen, such as in air, and up to nearly 100% oxygen).

To minimize the formation of potentially dangerous levels of $NO_2$ and other higher oxides of NO, particularly where relatively high concentrations of NO are being employed, the time the oxygen is in contact with the NO in the therapeutic gas should be minimized: the NO should be stored in the absence of $O_2$, and mixed with the $O_2$-containing gas shortly before the mixture is inhaled by the patient. In general, this means carrying out the mixing no more than about 10 minutes (preferably no more than about 5 minutes, and even more preferably no more than about 2 minutes) prior to inhalation of the therapeutic gas by the patient. It is recommended that the NO-containing gas and the $O_2$-containing gas be mixed immediately prior to inhalation, such as in a continuous flow apparatus as described below. The method can also include monitoring the concentration of NO and/or $NO_2$ in the therapeutic gas. Typically, the therapeutic gas will include no more than 5 ppm $NO_2$, and preferably no more than 1 ppm $NO_2$, at the point it is inhaled by the patient. If desired, at least a portion of any $NO_2$ which does form in the gas can be removed by exposing the therapeutic gas to an $NO_2$ scavenger prior to the patient's inhaling the gas.

A typical treatment protocol includes providing the therapeutic gas to the patient for at least one five-minute period per day for at least ten consecutive days, where the NO concentration is 40 to 240 ppm. This can be repeated several times each day. Another suitable treatment protocol includes providing the patient with a relatively low dose (e.g., 2 to 160 ppm) of NO in air or $O_2/N_2$ (e.g., 50% $O_2$) continuously for 8 hours or longer (e.g., 24 hours or even one week). Yet another protocol includes providing the patient with a high dose (e.g., 1000 ppm) of NO for a short period of time (e.g., less than 15 seconds) as needed to prevent sickling of the patient's erythrocytes, or to improve the oxygen-carrying capacity of the patient's hemoglobin. This might be accomplished using a portable multi-dose inhaler device equipped with a canister of compressed NO in an inert gas such as $N_2$, with or without a rebreathing tube. Since the therapeutic benefit appears to be long-lasting, it is expected that this high-dose treatment will not need to be repeated more than once per hour, and perhaps not more than once or twice per day. Generally, the therapeutic gas is provided to the patient for at least 10 seconds (e.g., long enough for one or two deep breaths), and up to 1 or 5 minutes). Since the blood volume of an adult is approximately 5 liters and the cardiac output is about 5 liters/minute, filling the lungs with the NO-containing gas for a minute would in theory result in treatment of the entire circulating blood volume (assuming complete mixing). A five minute duration of treatment would probably be a more realistic target. The optimal treatment protocol for any individual patient can readily be established by the patient's physician.

In a variation of the methods described above, the patient can be treated by administration of a therapeutically effective amount of an NO-releasing (or NO-donor) compound. Examples of suitable NO-releasing compounds include S-nitrosothiols such as S-nitroso-N-acetylpenicillamine, S-nitrocysteine, and others described in WO 92/17445 and U.S. Pat. No. 5,427,797 (herein incorporated by reference); nitroprusside; nitrosoguanidine; glyceryl trinitrate; azide; hydroxylamine; and any NONOate compound, including those disclosed in U.S. Pat. Nos. 4,954,526 and 5,155,137. Examples of NONOate compounds include diethylamine/NONO, diethylenetriamine/NONO, and methylaminohexylmethylamine/NONO (illustrated in Hanson et al., *Nitric Oxide, Biochemistry, Molecular Biology, and Therapeutic Implications*, Ignarro and Murad, Ed., Academic Press, New York (1995)). An NO-releasing compound can be provided in powder form or as a liquid (e.g., by mixing the compound with a biologically-compatible excipient). The NO-releasing compound can be administered to the patient alone or in conjunction with NO gas, CO gas, or another NO-releasing compound. When more than one compound is administered to the patient, the compounds can be mixed together, or they can be administered to the patient sequentially. Any one, or a combination, of the following routes of administration can be used to administer the NO-releasing compound(s) to the patient: intravenous injection, intraarterial injection, transcutaneous delivery, oral delivery, and inhalation (e.g., of a gas, powder or liquid). Inhalation is the preferred route of administration.

In yet another variation of the methods described above, the patient can be treated by contacting a portion of the patient's erythrocytes ex vivo or in situ with a therapeutically effective amount of gaseous NO and/or CO. For example, an extra-corporeal membrane oxygenator (ECMO) apparatus, a cardiopulmonary bypass (CPB) apparatus, or an intravenous oxygenator (IVOX) apparatus can be adapted for use in contacting the patient's erythrocytes with gaseous NO and/or CO (e.g., 1 to 1,000 ppm in an oxygen-containing gas).

In cases where the patient is identified as having SCD or one of the Hb-S combinations which produces sickling, the invention can be used to treat a patient identified as (i) suffering from sickle cell crisis, or (ii) being at risk of incurring a sickle cell crisis. For example, the patient may have SCD and be about to undergo surgery with general anesthesia. In such a case, the patient is treated according to the method of the invention during surgery, and/or within one hour before and/or after surgery, and for as long as deemed necessary to prevent the sickle cell crisis that often results from such surgery. The patients treatable with the invention include those with or without a known pulmonary disease (e.g., asthma or pulmonary hypertension) in addition to the hemoglobinopathy.

The reduced affinity of the patient's hemoglobin for oxygen can be measured as a rightward shift in the ODC of the patient's hemoglobin, relative to the ODC obtained with Hb-A. Alternatively, reduced affinity of the hemoglobin for oxygen can be measured as an increased $P_{50}$. value of the patient's hemoglobin, relative to the $P_{50}$ of Hb-A. If desired, the ODC and/or $P_{50}$ can be measured before and after treating the patient in order to provide an indication of the therapeutic effectiveness of the therapeutic gas, NO-releasing compound, or ex vivo erythrocyte treatment. A leftward shift in the patient's ODC, or a decrease in the patient's $P_{50}$ after treatment, relative to the ODC or $P_{50}$ before treatment, is an indication of the therapeutic effectiveness of the method. Another indication of the effectiveness of the treatment when NO is the therapeutic gas is the degree of Hb nitrosation, which can be measured, e.g., using the method of Kon et al., 1977, J. Toxicol. and Environmental Health 2:1109–1113 (herein incorporated by reference). For example, a level of 0.01% to 25% nitrosation can be taken as corresponding to a therapeutic effect. Alternatively, or in addition, the effectiveness of the treatment can be measured as a decrease in pain, which can be evaluated on an analog scale score (i.e., 0–10). If desired, the percent of abnormally-shaped (e.g., sickled and deformed) cells in the blood of the patient (with or without hypoxic or other stress that would be expected to produce sickling) can be determined before and after treatment; a decrease in the percent of abnormally-shaped cells after treatment provides an indication of the therapeutic effectiveness of the method.

As used herein, a "hemoglobinopathy" is a disorder or disease caused by, or associated with, the presence of an abnormal hemoglobin in the blood. Included are hemoglobinopathies in which a combination of abnormal hemoglobins are present in the blood (e.g., sickle cell/Hb-C disease). The hemoglobinopathies that can be treated with the method of the invention are associated with a reduced affinity of the patient's blood for oxygen, or a tendency of the patient's erythrocytes to sickle under hypoxic and other stresses.

A patient who is homozygous for Hb-S, the sickle cell hemoglobin in which valine is substituted for glutamic acid at the 6th position of the β chain of Hb-A, is said to have "sickle cell disease". "Sickle cell trait" is the heterozygous counterpart, in which only one of the patient's Hb-A genes is replaced with the mutant Hb-S gene. A patient with sickle cell trait typically has 20 to 45% Hb-S and the remainder Hb-A. In the homozygous state, 75–100% of the hemoglobin is Hb-S, and the rest of the hemoglobin is fetal hemoglobin (Hb-F) or Hb-$A_2$, both of which are expressed from different genetic loci than Hb-A or Hb-S. SCD causes all or a portion of the erythrocytes in the patient's peripheral blood to become abnormally shaped (e.g., sickle- or crescent-shaped) when exposed to certain triggering conditions such as low oxygen or dehydration. A patient with SCD occasionally will experience a sickle cell "crisis," characterized by vaso-occlusion which can affect nearly every organ of the body. Infarction (i.e., tissue necrosis due to a sudden insufficiency of blood supply) of bone, spleen, kidney, and lungs is common and results in severe pain and tissue death.

The hemoglobinopathy "Hb-C" is a condition characterized by the substitution of lysine for glutamic acid at the 6th position of the β chain of Hb-A. The hemoglobinopathy "Hb-D" results from the substitution of glutamine for glutamic acid at the 121st position of the β chain of Hb-A. "Hb-E" is characterized by the substitution of lysine for glutamic acid at the 121st position of the β chain of Hb-A. "Hb-H" is characterized by a homotetramer of the β chain. "Hb-I" results from the substitution of glutamic acid for lysine at the 16th position of the α chain. "Hb-Kansas" is characterized by the substitution of threonine for asparagine at the 102nd position of the β chain of Hb-A. These hemoglobinopathies can affect the plasticity and shape of erythrocytes containing the mutant hemoglobin, as well as their affinity for oxygen. The thalassemias result in less than a normal amount of β-globin being expressed from the affected locus, or expression of a mutant form of β-globin that is synthesized inefficiently or catabolized rapidly so that little is available for forming functional Hb. A patient who combines Hb-S with a β-thalassemia may have little or no normal Hb-A present to counteract the effects of the single Hb-S gene, and so may have the functional equivalent of SCD.

A "therapeutically effective" amount of gaseous NO, gaseous CO, or an NO-releasing compound is an amount or concentration sufficient to produce any one or more of the following: (i) a reduction in the $P_{50}$ of the patient's hemoglobin of at least 2 mm Hg; (ii) a statistically significant leftward shift in the patient's ODC; (iii) in the case of SCD, a 10% or greater decrease in the number of erythrocytes which deform under hypoxic conditions (defined as a $P_aO_2$ of less than 50 mm Hg); or (iv) in the case of a patient presenting in sickle cell crisis, a clinically significant decrease in the pain suffered by the patient at a time before one would have expected the crisis to resolve naturally.

The invention provides a simple, rapid, and efficacious method of treating a patient identified as having a hemoglobinopathy. Erythrocytes carrying normal hemoglobin are not significantly affected by the treatment method, at least at levels below 100 ppm NO and 35 ppm CO, so the method is safe to use even in heterozygotes. The therapeutic effects of the treatment (e.g., a reduction in $P_{50}$) persist even after the hemoglobin is no longer exposed to the source of NO or CO. In contrast to conventional methods for treating sickle cell crisis, which offer only supportive therapy, the invention can be used to prevent or reverse sickle cell crisis by reducing the polymerization of Hb-S and thus the formation of newly sickled cells. Because such sickling may be correlated with the level of pain, morbidity, and mortality resulting from sickle cell crisis, the invention mitigates the physical complications associated with SCD, in a non-invasive manner.

BRIEF DESCRIPTION OF THE DRAWINGS

FIG. 8 is graph showing that inhaled NO increases the affinity of RBCs for oxygen in SS patients (i.e., SCD patients). The average reduction of the RBC $P_{50}$ in ten studies with nine stable SS patients (□) was approximately 5 mm Hg (range 3–7 mm Hg; p<0.001) after the patients breathed 80 ppm NO for 45 minutes. In one SS patient, the RBC $P_{50}$ did not change. Normal adults (●) showed no change ($\leq 1$ mm Hg) in the RBC $P_{50}$ after breathing NO, indicating that the effects of NO are selective for patients having a hemoglobinopathy.

Figure 1:
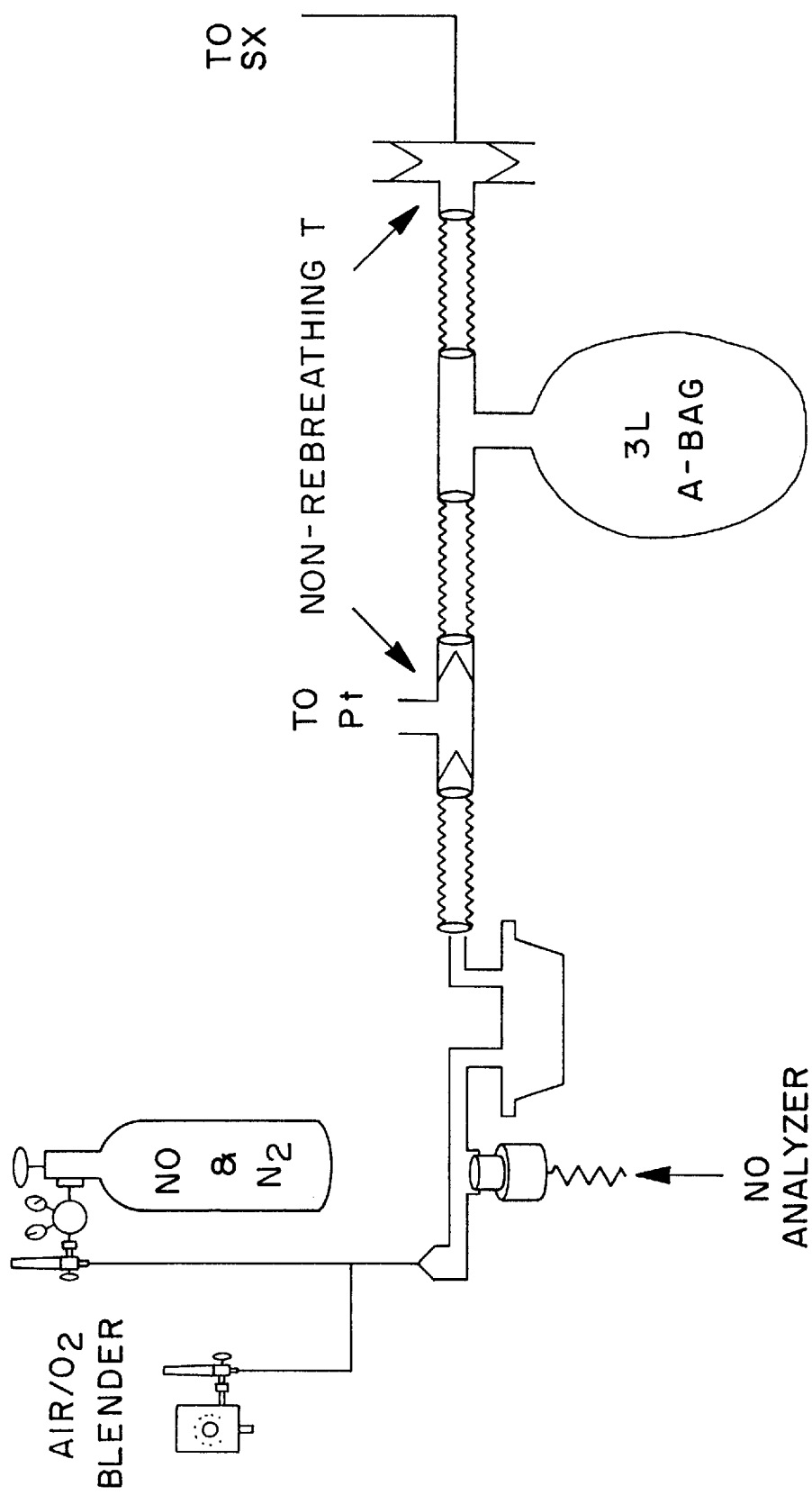
FIG. 1 is a schematic representation of a breathing circuit that can be used to provide the NO-containing therapeutic gas to a patient in a clinical setting.

Blood samples were taken from three AA and five SS patients while breathing air at one hour after NO breathing had been discontinued. The reduction in the RBC $P_{50}$ was maintained for at least one hour in 3 of 5 SS patients. In all patients, intraerythrocytic 2,3-DPG and ATP levels, venous pH and blood gas tensions did not change after 45 minutes of breathing nitric oxide. In all subjects, there were no clinical side effects noted. The mean methemoglobin level after 45 minutes of NO breathing was low (1.4±0.5%) for SS RBCs and the methemoglobin level returned to baseline after 60 minutes, even though the effects of NO therapy on oxygen affinity persisted in three of the five SS patients evaluated.

DETAILED DESCRIPTION

The methods of the invention can be used to treat a patient identified as having any of a variety of hemoglobinopathies characterized by a reduced affinity of the patient's hemoglobin for oxygen, compared with the affinity for oxygen of normal adult hemoglobin. This reduced affinity for oxygen is typically detected as a rightward shift in the ODC of the affected hemoglobin, compared to the ODC of Hb-A, or by an increase in the $P_{50}$ of the affected hemoglobin, compared to the $P_{50}$ of Hb-A. Such a reduced affinity for oxygen is characteristic of such abnormal hemoglobins as Hb-S (seen in the homozygous form as SCD, and in the heterozygous form as sickle cell trait), Hb-C, Hb-D, Hb-E, Hb-H, Hb-I, or Hb-Kansas disorder. A patient may be homozygous or heterozygous for the mutant gene. Occasionally a patient will be a "mixed heterozygote" who bears two different mutant β-globin genes. Examples include the following combinations: S/C, S/D, S/b-Arab, S/Quebec-Chori, S/β-thalassemia, S/E, S/Lepore, and others described in Kinney and Ware, Compound Heterozygous States, Chapter 29 in *Sickle Cell Disease: Basic Principles and Clinical Practice*, Ed. Stephen H. Embury et al., Raven Press, Ltd., New York (1994), herein incorporated by reference. Conventional methods and criteria, including clinical observations, genetic analysis, protein analysis, ODC analysis, and $P_{50}$ analysis, can be used to identify a patient having such a hemoglobinopathy, including patients with yet-to-be discovered types of hemoglobinopathies. Described below are simple in vitro tests useful for determining whether a given hemoglobinopathy is likely to respond to treatment with the methods of the invention. Alternatively, one could test the method directly in the patient.

Use of Inhaled Gaseous NO or CO to Treat a Hemoglobinopathy

In one aspect of the invention, gaseous NO or CO, or a combination of NO and CO, is provided to a patient for inhalation. The use of NO is described below; similar principles apply to the use of CO or a combination of CO and NO. Compressed NO gas or CO gas can be obtained from a commercial supplier, such as Airco (Murray Hill, N.J.) or Air Products and Chemicals, Inc. (Allentown, Pa.). Typically, NO is provided as a mixture of 200–2000 ppm NO in $N_2$ or another inert gas such as helium. It is preferable to store the NO as a mixture that is free of $O_2$, because $O_2$ can react with NO to form toxic higher oxides of nitrogen such as $NO_2$. If desired, the NO-containing gas can be mixed with air or $O_2$ immediately prior to providing the mixture for inhalation. Calibrated rotameters that have previously been calibrated with a spirometer can be used to mix precise amounts of the NO-containing gas with air or $O_2$, particularly in a hospital setting. Generally, a therapeutic gas that includes at least 21% oxygen as well as a therapeutic level of NO and/or CO is suitable for use in the invention. The concentration of CO can be determined, if desired, using standard infrared detection techniques. In order to limit the formation of higher oxides of nitrogen, the NO should be in contact with oxygen for less than about 10 minutes (and preferably less than 5 minutes) prior to inhalation of the therapeutic gas by the patient. If desired, standard chemiluminescence methods can be used to measure the amount of NO and/or $N_2$ in the therapeutic gas prior to administering the gas to a patient (see, e.g., Fontijin et al., 1970, Anal. Chem. 42:575–579). $NO_2$ can be scavenged prior to providing the therapeutic gas to the patient. Appropriate scavenging methods include exposing the gas to NaOH solutions, baralyme, or soda lime. These scavenging methods can also be used to extract $NO_2$ from the gas that is exhaled by the patient, if desired, so the $NO_2$ is not introduced into the atmosphere.

The preferred way to supply the therapeutic gas to the patient is by continuous flow, e.g., in a mask-breathing circuit, rather than static mixing in a receptacle such as a Douglas bag. An exemplary breathing circuit is shown schematically in FIG. 1. This circuit includes a source of a pressurized mixture of gaseous NO in $N_2$, a source of air or $O_2$ gas connected to a blender for introducing the air or $O_2$ into the circuit, a NO analyzer for monitoring the concentration of NO in the therapeutic gas, and a non-rebreathing T valve leading to the patient. The exhaled gases can be scavenged, if desired, by the hospital's vacuum system. The concentrations of NO and $NO_2$ within the breathing circuit can be analyzed electrochemically with commercially available sensors (e.g., Exidyne Instrumentation Technologies NO sensor (model no. 4586) and $NO_2$ sensor (model no. 4584); Exton, Pa.). The oxygen concentration can be monitored with an in-line oxygen analyzer, if desired.

As an alternative to using a mask-breathing circuit, a portable inhaler device (with or without a rebreathing tube) can be used to provide the NO to the patient. Examples of suitable inhaler devices that could be adapted for the methods of the invention are described in WO 92/10228, and in U.S. Pat. Nos. 5,485,827, 5,396,882, 4,667,668; 4,592,348; 4,534,343; and 4,852,561; each of which is herein incorporated by reference. Other inhaler devices are described in the *Physicians' Desk Reference*, Edward R. Barnhar, Publisher. Generally, suitable inhaler devices are portable, i.e., less than 5 kg, and preferably less than 1 kg, and may be of a design similar to those inhalers currently available for the treatment of asthma attacks. The device contains either or both of (a) pressurized NO or CO gas, and (b) a NO-releasing compound. Typically, such a device would include a pressurized gas containing at least 1 ppm (preferably at least 5 ppm, more preferably at least 40 and most preferably at least 80 ppm) NO or CO. The concentration of NO or CO in the pressurized gas can be relatively high, e.g. 160, 300, 500, or 1000 ppm. It is contemplated that concentrations as high or even higher than 1500 ppm or 2000 ppm could be used. If desired, the device can contain a mixture of pressurized NO gas and either an inert gas such as $N_2$, or a liquid propellant such as a fluorocarbon, e.g., freon.

Prior to administering the therapeutic gas to the patient, the patient's blood can be analyzed, if desired, in order to establish a baseline against which the NO-treated blood can be compared. Typically, a 10 ml sample of blood will be drawn into a heparinized syringe, and the hemoglobin, hematocrit, oxygen saturation, and/or methemoglobin saturation measured. The ODC, $P_{50}$, and/or level of nitrosation of the patient's hemoglobin; and/or the erythrocyte 2,3-diphosphoglycerate concentration can be measured before the therapeutic gas is inhaled. Also, an aliquot of the blood sample can analyzed for degree of erythrocyte sickling. Any or all of these parameters can be measured again following inhalation of the therapeutic gas to provide a measure of the therapeutic effectiveness of the inhaled gas. If desired, the patient's blood oxygen saturation can be monitored by pulse oximetry while the patient breathes the therapeutic gas. If desired, additional blood samples can be drawn over time, as the patient continues to breathe the therapeutic gas.

Typically, the patient will breathe the therapeutic gas for at least 1 minute, and usually for 5 to 30 minutes where levels of NO below 500 ppm are being employed (e.g., 80 ppm). The lower the concentration of NO, the longer the inhalation period can be; e.g., inhalation can be continuous for over 24 hours at a relatively low level of 40 or 80 ppm. Higher levels of NO can be used for short periods of time. If no toxicity (e.g., in the form of significant (over 10%) methemoglobinemia) is detected, the use of such higher levels can be extended or repeated as needed over the course of a day. It is envisioned that some hemoglobinopathies may benefit from regular prophylactic treatment with NO or CO, e.g., three or more times daily throughout the patient's lifetime, with additional treatments whenever the risk of a crisis is high.

It is expected that CO can be used at a concentration of 50–100 ppm for indefinite periods of time, and higher concentrations (e.g., 200–500) for intermediate periods (such as an hour). When CO and NO are used in combination, Co might be used at a concentration of 1–100 ppm, and NO at a concentration of 1–80 ppm, though higher or lower doses can be employed where warranted.

While the optimal therapeutic regimen for any given patient depends on factors such as the type of hemoglobinopathy suffered and the severity of the disease condition when the patient presents, a typical suitable therapy regimen involves breathing a therapeutic gas (containing 2 to 160 ppm NO or CO) for at least one 5 minute period per day for at least 10 consecutive days. Alternatively, the patient might breathe a much higher concentration of NO or CO (e.g., 300–2000 pm) for a shorter time (e.g., as short as a single breath) from once to several times per day, as needed. Where the patient is in sickle cell crisis, it is expected that high levels of NO will be needed continuously on an emergency basis until the immediate crisis has passed. A patient at significant risk of incurring a sickle cell crisis (e.g., during an expected hypoxic exposure) should be maintained on a level of NO or CO adequate to prevent or at least reduce the severity of the crisis, as long as the risk remains. Because a sickle cell disease patient who has to undergo surgery (e.g., to remove a damaged spleen) is at high risk of incurring a crisis during or immediately after surgery, it is recommended that such patients be provided with the therapeutic gas during and after surgery, and preferably immediately before surgery as well (to load the patient's hemoglobin with NO).

Use of an NO-releasing Compound to Treat a Hemoglobinopathy

In lieu of, or in addition to, employing gaseous NO or CO, an NO-releasing compound can be used to deliver a therapeutically effective amount of NO to the patient's hemoglobin. Examples of suitable NO-releasing compounds include S-nitrosothiols such as S-nitroso-N-acetylpenicillamine (SNAP), and S-nitrocysteine; nitroprusside; nitrosoguanidine; glyceryl trinitrate; azide; hydroxylamine; and any NONOate compound. The criteria for selecting additional NO-releasing compounds include their stability in storage prior to inhalation, and their ability to decompose to release NO at a therapeutically beneficial rate upon injection, oral delivery, or deposition in the appropriate part of the respiratory tract. For example, SNAP has been shown to be stable in its solid form, but under physiological conditions (such as in the film of physiological fluid on the surface of the bronchiolar or alveolar lumen), the compound readily decomposes to release NO (Ignarro, Circ. Res. 65:1–21, 1989).

An NO-releasing compound can be administered to the patient by any of a variety of routes, including intravenous injection, intraarterial injection, transcutaneous delivery, oral delivery, or inhalation. For inhalation, the NO-releasing compound can be packaged into an inhaler device, such as one of the devices described above, or it can be delivered via a breathing circuit such as the one described above. To facilitate delivery, the NO-releasing compound can be dissolved in a biologically-compatible excipient (e.g., water or saline). Alternatively, the NO-releasing compound is inhaled in solid or liquid form, the particles or droplets are deposited throughout the respiratory system, with larger particles or droplets tending to be deposited near the point of entry (i.e., the mouth or nose) and smaller particles or droplets being carried progressively farther into the respiratory system before being deposited into the trachea, bronchi, and finally the alveoli. (See, e.g., Hounman & Morgan, "Particle Deposition," Ch. 5 in *Respiratory Defense Mechanisms, Part* 1, Marcel Dekker, Inc., NY; ed. Brain et al., 1977, p. 125). A particle/droplet size of 10 μm or less is recommended for use in the invention.

The optimal dosage of an NO-releasing compound for any given patient can readily be determined, and will depend on factors such as the nature of the compound, the type of hemoglobinopathy, and the severity of the disease condition. Where the NO-releasing compound is provided for inhalation, it may be in solid or liquid form. A typical dosage for an adult would be about 1–5 mg, regardless of delivery route.

Use of NO Ex Vivo or In Situ to Treat a Hemoglobinopathy

In order to deliver NO or CO to a patient's blood ex vivo or in situ, one could adapt a standard ECMO, IVOX, or CPB apparatus to use a gas containing not only $O_2$ but also NO and/or CO at a therapeutically effective concentration. Typically, the patient's blood is withdrawn continuously from the patient and pumped through the ex vivo gas exchanger, then returned to the patient. As the blood passes by the gas-permeable membrane separating it from the therapeutic gas, NO or CO molecules which have been absorbed through the membrane enter the blood and then interact with the hemoglobin in the erythrocytes. In situ gas exchangers such as IVOX are placed directly into the patient's vasculature, rather than requiring that the blood be pumped out of the body. Other types of devices not specifically designed for delivery into the blood, but which could be adapted for the delivery of NO into the blood of a patient in need of same, are described in co-owned application USSN 08/036,522, herein incorporated by reference.

In Vitro Tests

The experiments discussed below demonstrate that exposure of Hb-S erythrocytes to non-toxic levels of NO causes a leftward shift in the ODC and a decrease in the $P_{50}$ of the hemoglobin, indicating that NO therapy alters the ability of the abnormal hemoglobin to bind and release oxygen so that it more closely resembles Hb-A. During NO therapy, the $PO_2$ at which the abnormal hemoglobin desaturates (i.e., gives up its $O_2$ molecule) decreases. Thus, the ratio of unsaturated to saturated Hb-S at a given partial pressure of oxygen is reduced during NO therapy. Since Hb-S is less likely to polymerize if it is bearing $O_2$, the likelihood that Hb-S will polymerize at a given $O_2$ partial pressure is reduced during NO therapy, with a concomitant decrease in erythrocyte sickling. In addition, the data discussed below suggest that NO therapy may directly affect heme-heme interactions or cause a conformational change in the Hb-S (possibly by forming an NO adduct), decreasing the tendency of Hb-S to polymerize independent of its effect on the ODC of Hb-S. Thus, treatment with NO is believed to have an additional beneficial effect in preventing Hb-S polymerization and erythrocyte sickling independent of its effect on oxygen affinity, so that even when the NO-treated Hb-S gives up its $O_2$, the erythrocytes still do not sickle as readily.

EXPERIMENT I

NO Causes a Reduction in the $P_{50}$ of Abnormal Hemoglobin

Figure 2:
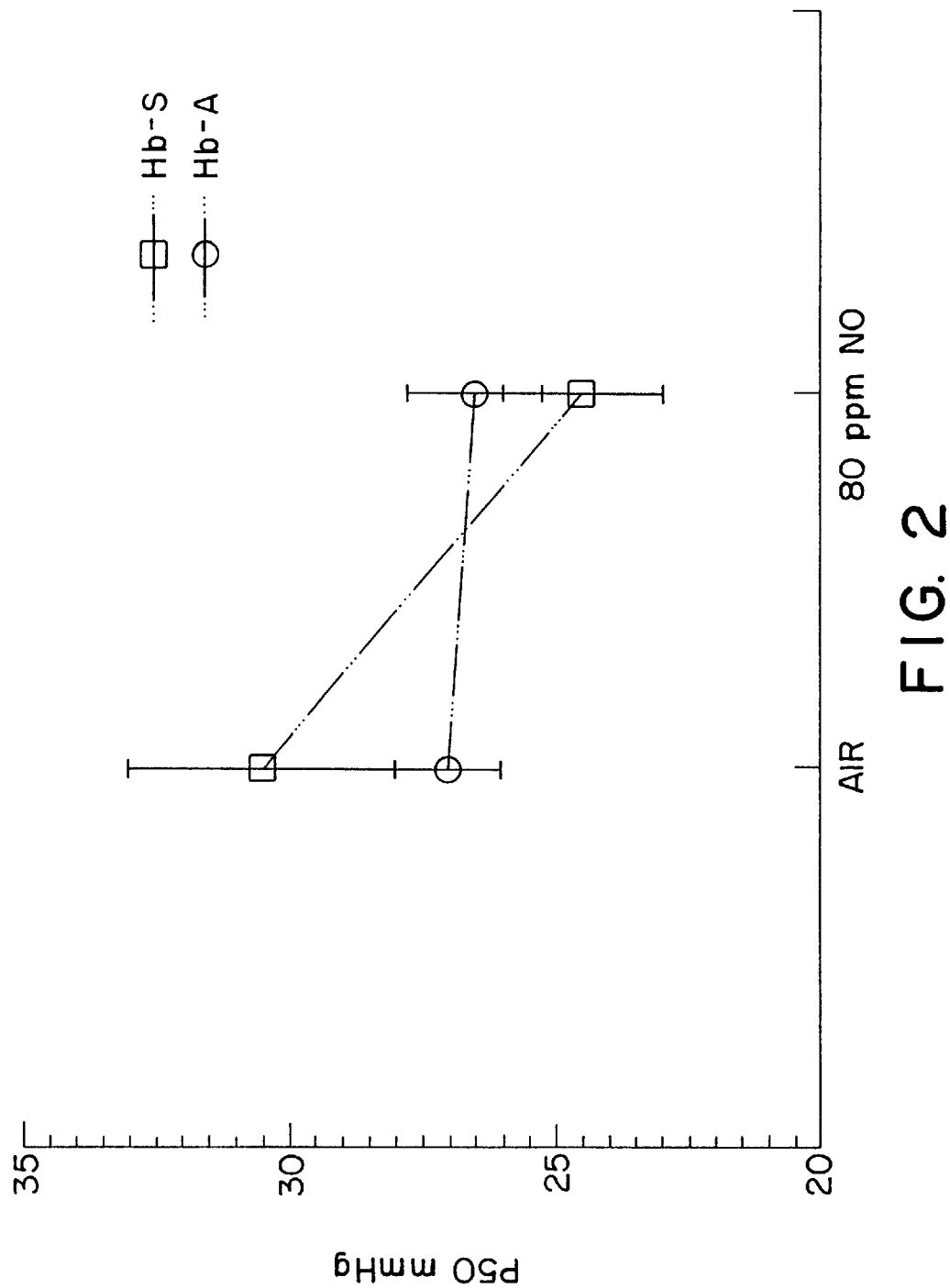
FIG. 2 is a graphic representation of the $P_{50}$ of whole, fresh human Hb-A and Hb-S erythrocytes after in vitro exposure to air without NO, or after exposure to 80 ppm NO in air.
Figure 3:
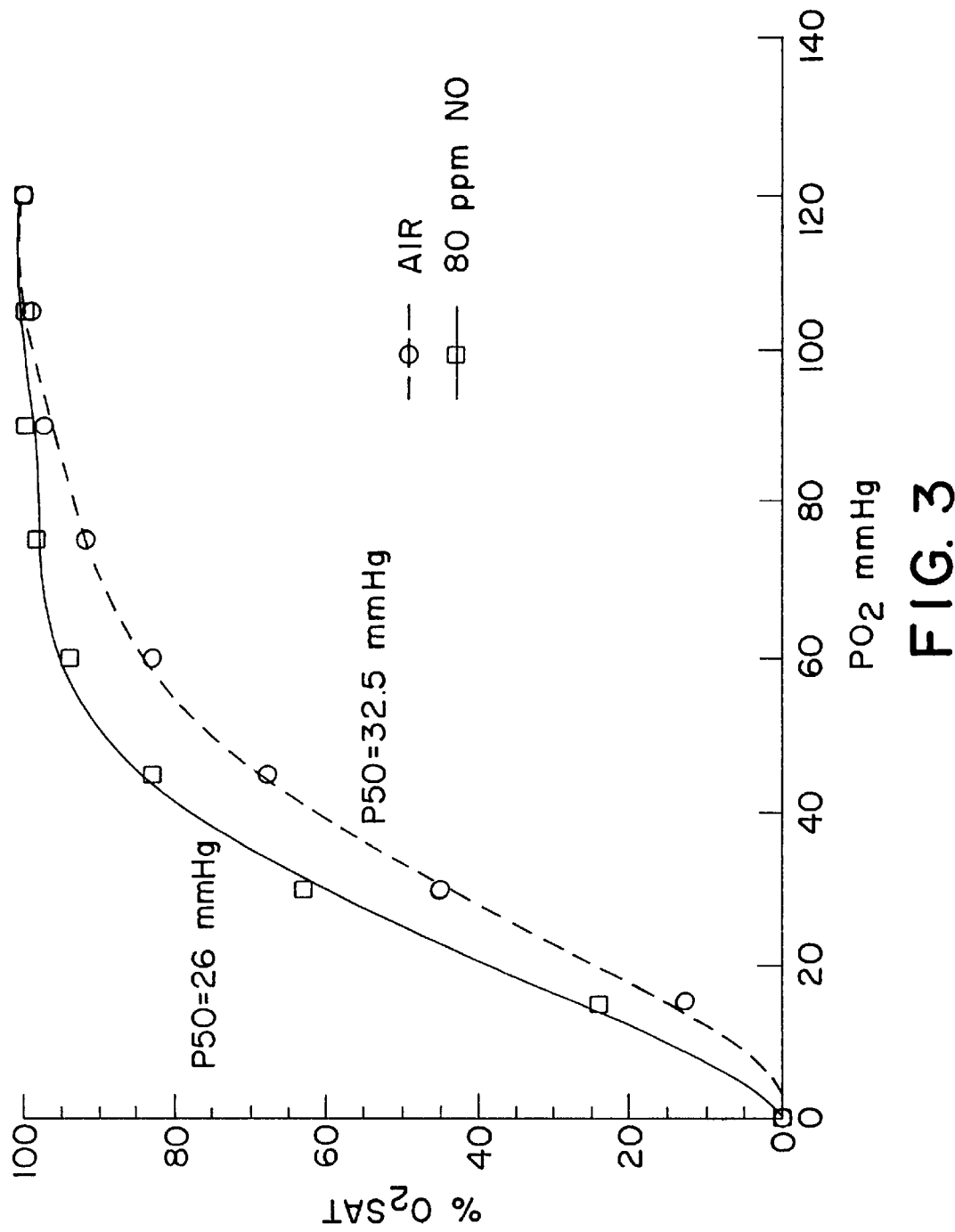
FIG. 3 is a graphic representation of the ODC and $P_{50}$ of human Hb-S erythrocytes in air and in 80 ppm NO in air in vitro. NO treatment causes a leftward shift in the ODC and a decrease in the $P_{50}$ of Hb-S erythrocytes.

This experiment demonstrates that exposure of erythrocytes to non-toxic levels of NO reduces the $P_{50}$ (i.e., causes a leftward shift in the ODC) when the cells contain Hb-S, but not when they contain solely normal Hb-A. Freshly drawn human erythrocytes from either SCD patients or normal controls were washed in standard Colin's solution and exposed to 80 ppm gaseous NO in air for 15 minutes, using a blood/gas tonometer. Using an automatic blood oxygen dissociation analyzer, the ODC of the hemoglobin was measured both before and after exposure of the erythrocytes to NO. As is illustrated in FIG. 2, exposure of normal erythrocytes (Hb-A) to 80 ppm NO under these conditions does not result in a significant change in the Hb-A $P_{50}$ value of 26 mm Hg. In contrast, exposure of Hb-S to 80 ppm NO in air causes a significant reduction in the Hb-S $P_{50}$ value compared to the Hb-S $P_{50}$ in air alone. As illustrated in FIG. 2 and in the ODC shown in FIG. 3, the $P_{50}$ of a sickle cell patient's red cells containing Hb-S (and possibly other hemoglobins, e.g., Hb-C) in air was 32.5 mm Hg, while the $P_{50}$ after exposure to NO was reduced to 26 mm Hg. These data also indicate that, as expected, the $P_{50}$ without NO exposure of red cells containing Hb-S (30.5 mm Hg) was elevated, relative to the $P_{50}$. without NO exposure of red cells containing Hb-A (27 mm Hg). As shown in Table 1, the NO exposure induced a decrease in the $P_{50}$ of Hb-S erythrocytes which persists for at least one hour after NO treatment is discontinued. Other experiments show this decrease persisting for at least two hours.

TABLE 1

| Sequential Exposure of HB-S RBC | $P_{50}$ |
|---|---|
| Air (baseline) | 35 mm Hg |
| Air with 80 ppm NO × 15 minutes | 30 mm Hg |
| Air × 15 minutes, after NO off | 30 mm Hg |
| Air × 30 minutes, after NO off | 30 mm Hg |
| Air × 60 minutes, after NO off | 30 mm Hg |

EXPERIMENT II

Effect of Length of Exposure to NO on the $P_{50}$ of Hb-S RBC

This experiment illustrates that an exposure to 80 ppm NO in a tonometer for less than five minutes is sufficient to cause a significant reduction in the $P_{50}$ of cells containing Hb-S. Samples of erythrocytes from two different patients with SCD were exposed to 80 ppm NO or to air, for various lengths of time (1, 5, 30, and 60 minutes), and the $P_{50}$ values were determined.

Figure 4:
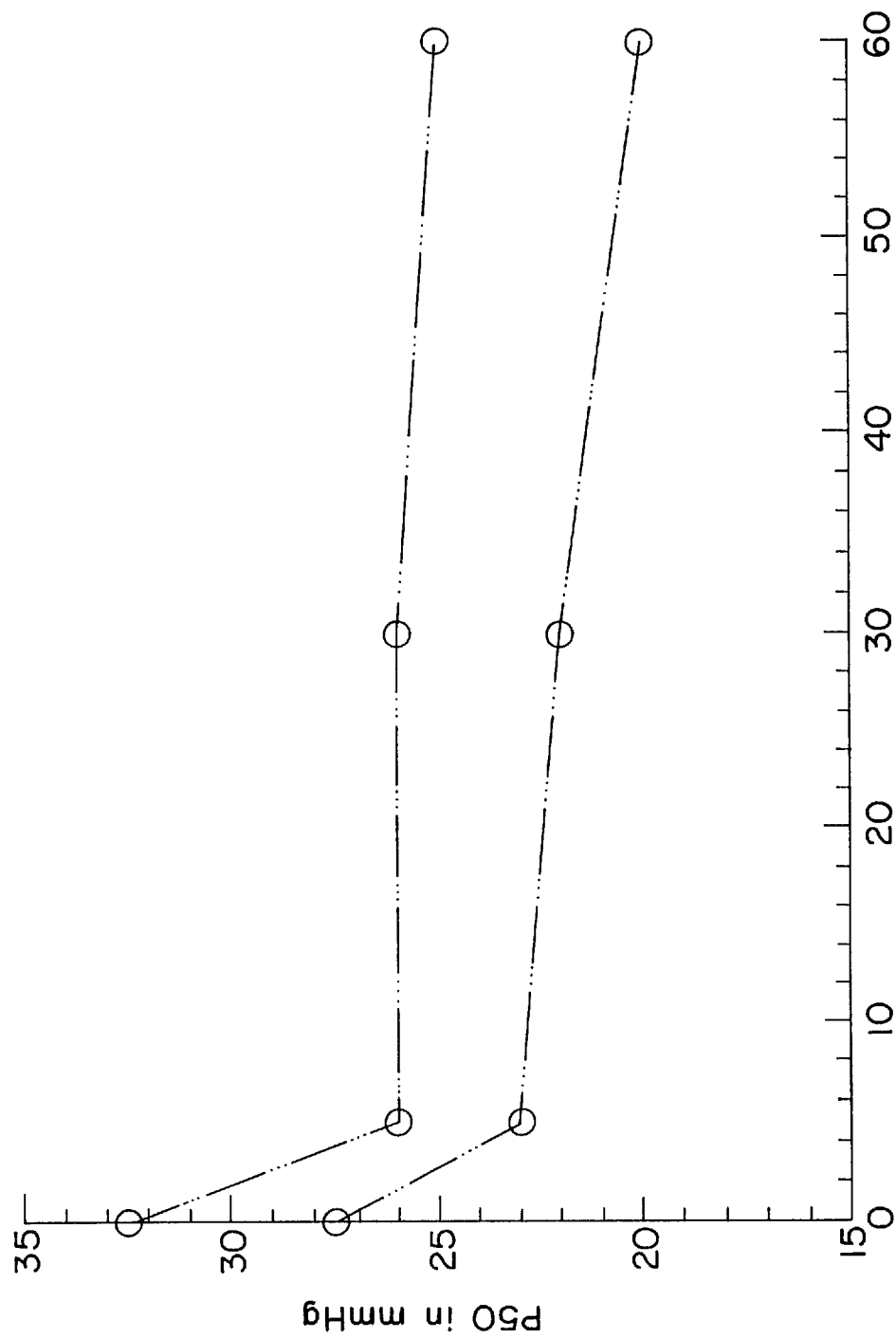
FIG. 4 is a graphic representation of the $P_{50}$ of human Hb-S erythrocytes after in vi tro exposure to 80 ppm NO in air for various lengths of time (data from two patients are shown). Five minutes of NO treatment significantly reduces the $P_{50}$ of Hb-S, while further NO treatment has little if any additional effect.

Although exposure of Hb-S erythrocytes to 80 ppm NO for 1 minute did not substantially alter the $P_{50}$ of these cells (FIG. 4), exposure of Hb-S erythrocytes to 80 ppm NO for as little as 5 minutes led to a significant reduction in the $P_{50}$ for the samples from both patients (shown as separate lines in FIG. 4). Exposing the erythrocytes to 80 ppm NO for 30 or 60 minutes maintained the observed reduction but did not cause a significant further reduction in the $P_{50}$ beyond that observed with a 5 minute exposure. Exposing the Hb-S-containing erythrocytes to air without NO for up to 60 minutes produced no significant change in the $P_{50}$ over time (data not shown).

EXPERIMENT III

Effect of Oxyhemoglobin Concentration on the Ability of NO to Alter $P_{50}$

This experiment illustrates how the oxyhemoglobin concentration affects the ability of NO to reduce the $P_{50}$ of Hb-S. In these experiments, two flasks containing human Hb-S erythrocytes were incubated in a 37° C. water bath. The $O_2$ concentration of the gas in each flask was decreased in steps at one hour intervals from 20% to 16%, 12%, 8%, 4%, and then 0% $O_2$. One set of flasks also contained 80 ppm NO throughout the experiment, and both sets contained 5% $CO_2$ throughout the experiment. Samples of erythrocytes were removed from each flask after each hour (i.e., with each reduction in oxygen concentration). The concentrations of oxyhemoglobin and methemoglobin were determined by multiwavelength oximetry (using a Ciba-Corning Co-Oximeter Model 270 apparatus and conventional methods). Cell morphology was evaluated using light microscopy to determine the percentage of normal, deformed, and sickled erythrocytes in each sample. Deformed cells are defined as cells which do not have the typical shape of either normal cells or sickled cells.

Figure 5:
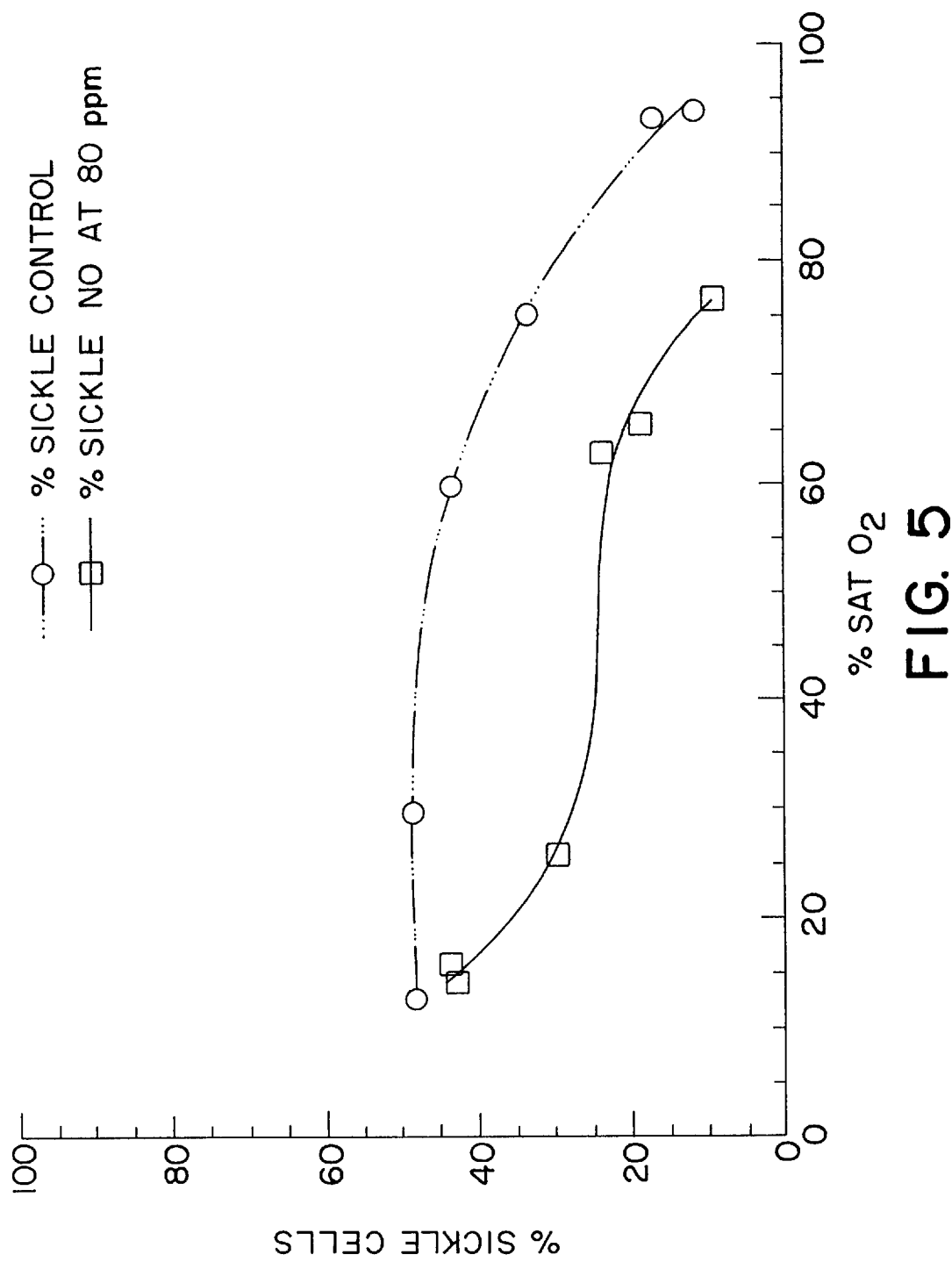
FIG. 5 is a graphic representation of the percentage of sickled human Hb-S erythrocytes as a function of percent hemoglobin saturation with oxygen, in the presence of air or 80 ppm NO. In vitro NO treatment (80 ppm) decreases the percentage of sickled cells at all oxyhemoglobin concentrations.
Figure 6:
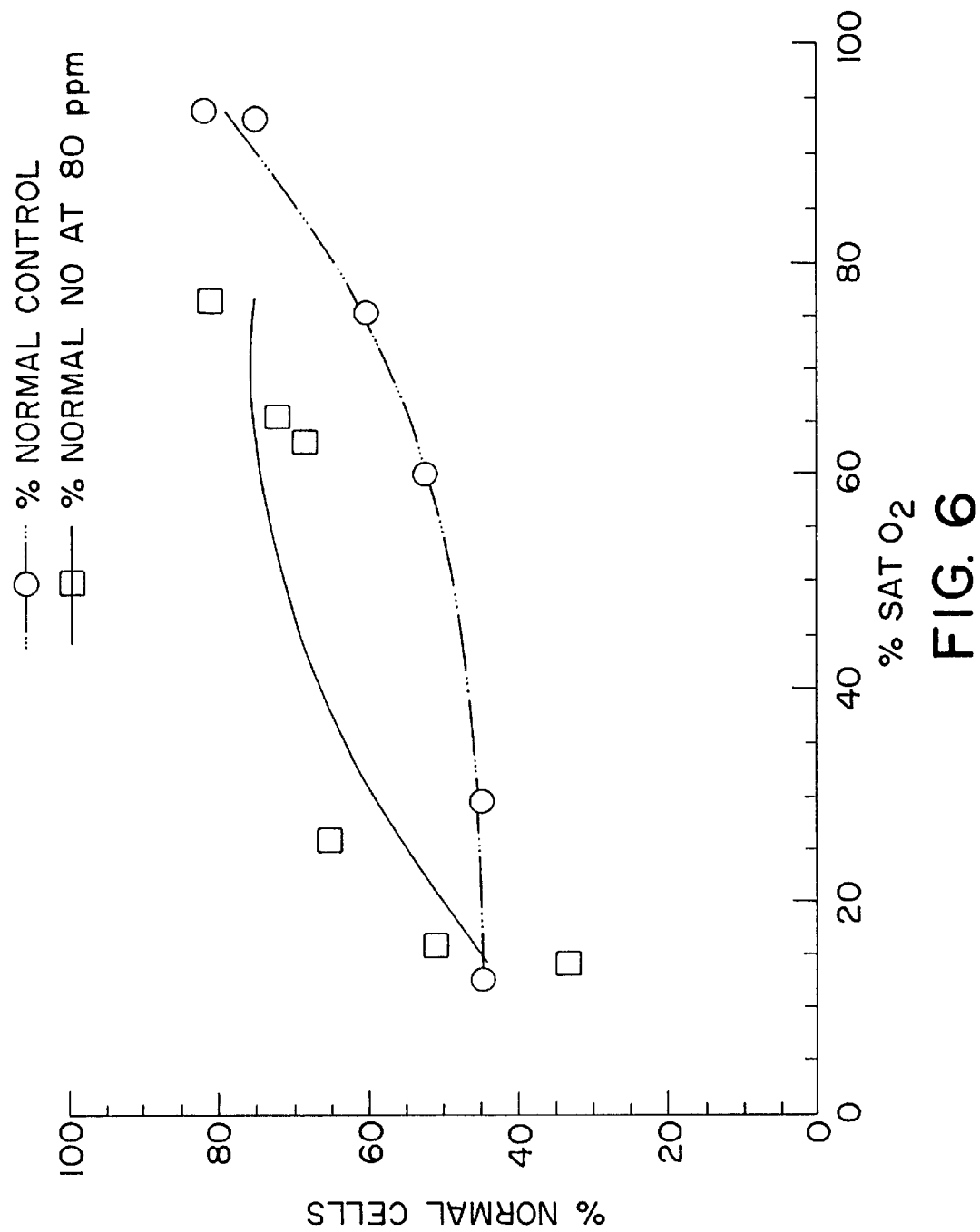
FIG. 6 is a graphic representation of the percent of normal-appearing cells (as opposed to deformed cells or sickled cells) as a function of percent hemoglobin saturation with oxygen, in the presence of air or 80 ppm NO in air. More of the NO-treated cells had a normal appearance than did cells that were exposed only to air.

As illustrated in FIG. 5, NO treatment decreases the percentage of sickled cells at all oxyhemoglobin concentrations. The NO-exposed erythrocytes incurred 10%–15% less sickling than the control erythrocytes at the same percent hemoglobin oxygen saturation. This suggests that 80 ppm NO may alter "heme-heme" interactions or produce a conformational change of the abnormal hemoglobin molecule in a way which is independent of the effect on oxygen affinity, reducing the tendency of the Hb-S to polymerize at a given oxygen saturation. Furthermore, a higher percentage of the NO-treated cells than the control cells were judged to be "normal" (as opposed to deformed or sickled) at each percent hemoglobin oxygen saturation measured (FIG. 6).

EXPERIMENT IV

Dose Response

Figure 7:
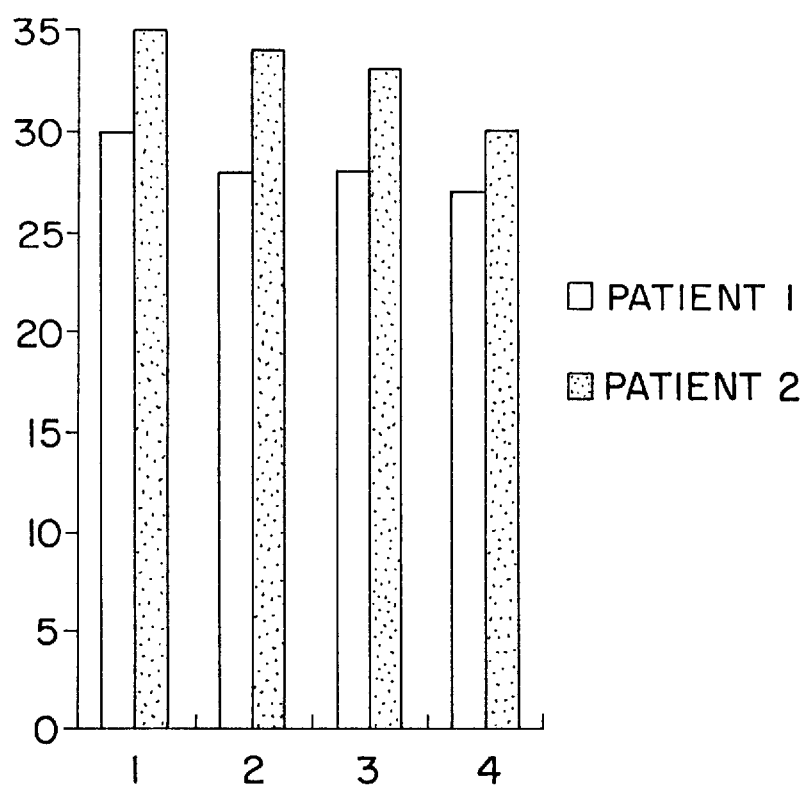
FIG. 7 is a bar graph illustrating the progressive decrease in $P_{50}$ when erythrocytes obtained from two patients with SCD were treated in vitro with escalating concentrations of NO in air. 1=0 ppm NO; 2=10 ppm NO; 3=40 ppm NO; 4=80 ppm NO.

This experiment illustrates that increasing NO concentrations produce an increasing effect on $P_{50}$ of erythrocytes containing Hb-S. Samples of erythrocytes from two different patients with SCD were exposed to air (0 ppm NO; illustrated in column 1 in the FIG. 7 bar graph), or to 10 ppm NO (column 2), 40 ppm NO (column 3), or 80 ppm NO (column 4) for 5 minutes. The $P_{50}$ values were then determined. As shown in FIG. 7, the $P_{50}$ values for the erythrocytes from each patient decreased with increasing NO concentration.

In Vivo Tests in Humans

The experiments discussed below demonstrate that inhalation of NO increases the affinity of RBCs for oxygen in human patients diagnosed as having SCD. Thus, NO alters the ability of the abnormal hemoglobin to bind and release oxygen so that it more closely resembles Hb-A. In these studies, the patients were three normal male adults ages 25–40 years (referred to herein as "AA") and nine (seven male and two females) clinically stable adults (ages 20–33 years) who were homozygous for Hb-S (referred to herein as "SS").

Briefly, in SCD subjects, these experiments show that breathing NO at 80 ppm in air decreased the partial pressure of oxygen at which the hemoglobin is 50% saturated with oxygen. Even at 60 minutes after discontinuing breathing NO, the $P_{50}$ continued to be decreased. Details of these experiments follow.

ODC determinations

Fifty microliters of whole blood were obtained by venipuncture from AA or SS adults and diluted with 4 ml of phosphate buffer, 10 μl antifoam solution and 20 μl 20% albumin. The blood samples were desaturated by exposure to 100% nitrogen ($N_2$) gas and then reoxygenated with air using a Hemox analyzer (TCS Medical Products Company, Huntingdon Valley, Pa.) to measure the ODC using conventional methods (Guarnone et al., 1995, Haematologica, 80:426–430). The $P_{50}$ was determined as the partial pressure of oxygen at 50% oxyhemoglobin saturation. To ensure the accuracy of repeated measurements over time using SS RBCs, blood samples obtained for three SS patients were measured at 0, 15, 30 and 60 minutes without NO gas exposure; changes in $P_{50}$ were not detected.

NO Inhalation in SS and AA Adults

Three normal and nine SCD adults were studied. One SS patient was studied twice, with one month's time interval between studies. Blood pressure, electrocardiograms, respiratory and heart rates, and pulse oximetry were continuously monitored. Subjects breathed air and then 80 ppm NO in air via a non-rebreathing circuit for 45 minutes. Venous blood was sampled before and immediately after NO breathing. The normal subjects and five SCD patients had an additional blood sample drawn one hour after NO breathing. ODCs were measured ex vivo, as described above.

In addition, the concentrations of adenosine triphosphate (ATP) and 2,3-diphosphoglycerate (DPG) in RBCs were determined using standard methods (Poillon et al., 1985, J. Biol. Chem 260:13897–13900). Methemoglobin was measured using a CO-Oximeter (Ciba-Corning Model 270, Mayfield, Mass.) and standard techniques before and after exposure of RBCs to NO. Venous pH and blood gases were measured using a pH/blood gas analyzer (Ciba-Corning Model 170, Mayfield, Mass.) and standard techniques.

Statistical Analysis

The data presented below are expressed as mean ±SEM, except where indicated. Both paired and unpaired Student's t-Tests were used, with a P value of less than 0.05 indicating statistical significance. All tests were two-tailed. Correlations were evaluated by computing the Pearson correlation coefficient.

NO Inhalation in SS and AA Adults

To show that low concentrations of NO alter Hb-S in vivo, the $P_{50}$ in RBCs from AA and SS patients was measured before and after the patients breathed 80 ppm NO in air for 45 minutes. In SS patients who breathed 80 ppm NO, the RBC $P_{50}$ was decreased (P<0.001), with an average reduction of 4.6±2 mm Hg (FIG. 8). In contrast, the RBC $P_{50}$ of AA patients who breathed NO did not change (≦1 mm Hg; P=NS), indicating that the effect of NO is selective for RBCs of patients having a hemoglobinopathy. The SS patient who was studied twice (with one month between studies) had a significant reduction in P50 on both occasions. In sum, these data show that breathing NO increases the affinity of hemoglobin for oxygen in RBCs of patients who have sickle cell disease.

To demonstrate that breathing NO affects $P_{50}$ even after the nitric oxide therapy is discontinued, the ODC of five SS patients was measured one hour after NO inhalation was discontinued. In three of the five patients, the RBC $P_{50}$ remained decreased, indicating that the effect of NO on the oxygen affinity of SS RBCs persists after NO is discontinued (FIG. 8).

For all patients who breathed 80 ppm NO in air for 45 minutes, the concentrations of ATP and 2,3-DPG in the patients' RBCs did not change in response to NO. In addition, the patients' blood pressure, respiratory and heart rates, transcutaneous oxygen saturation levels ($S_PO_2$), venous blood pH, and electrocardiogram data were unchanged during NO breathing. Patients with SS RBCs had a higher baseline methemoglobin level (0.5±0.2%) than did patients with AA RBCs (0.1±0.1%). Exposure to NO led to a small increase in methemoglobin levels in both SS RPCs (1.4±0.7%) and AA RBCs (0.7±0.1%); at 60 minutes after NO exposure, these methemoglobin levels returned to nearly baseline levels (0.6±0.3% and 0.2±0.1%, for SS and AA patients, respectively). There was no correlation between the increase in methemoglobin levels and the decrease in $P_{50}$ values (r=0.02, n=10). In fact, the shift in $P_{50}$ persisted at 60 minutes after NO exposure in three of five SS patients tested, while the methemoglobin levels had returned to baseline values. In sum, these data show that NO can be administered at therapeutically effective levels without leading to significant methemoglobin levels and without causing significantly detrimental consequences to the patients' vital statistics.

Summary

The in vitro and in vivo experiments described above demonstrate that the affinity of oxygen for hemoglobin increases when SS RBCs are exposed to low concentrations of nitric oxide. This increased affinity for oxygen persisted for at least two hours in vitro and at least one hour in vivo after ceasing administration of nitric oxide. These therapeutic effects of NO treatment were obtained without producing clinically significant levels of methemoglobin. Thus, these data show that inhalation of gaseous nitric oxide can be an effective therapy for treating hemoglobinopathies that are characterized by (a) a decreased affinity of the patient's hemoglobin for oxygen compared with the affinity for oxygen of normal adult hemoglobin, or (b) a tendency of the patient's erythrocytes to sickle.

Other embodiments are within the following claims.

What is claimed is:

1. A method of treating a patient identified as having a hemoglobinopathy, which method comprises identifying a patient having a hemoglobinopathy characterized by (a) a reduced affinity of the patient's hemoglobin for oxygen compared with the affinity for oxygen of normal adult hemoglobin (Hb-A), or (b) a tendency of the patient's erythrocytes to sickle; and administering a therapeutic gas to the patient, wherein the therapeutic gas comprises a therapeutically effective amount of gaseous nitric oxide (NO).

2. The method of claim 1, wherein the therapeutic gas contains NO at a concentration of at least 1 ppm.

3. The method of claim 2, wherein the therapeutic gas contains NO at a concentration of at least 10 ppm.

4. The method of claim 3, wherein the therapeutic gas contains NO at a concentration of 40–2000 ppm.

5. The method of claim 1, wherein the therapeutic gas is provided to the patient for at least 10 seconds.

6. The method of claim 5, wherein the therapeutic gas is provided to the patient for at least 5 minutes.

7. The method of claim 1, wherein the hemoglobinopathy is sickle cell disease.

8. The method of claim 7, wherein prior to administering the therapeutic gas, the patient is diagnosed as suffering from sickle cell crisis.

9. The method of claim 7, wherein prior to administering the therapeutic gas, the patient is identified as being at risk of incurring a sickle cell crisis.

10. The method of claim 1, wherein the hemoglobinopathy is selected from the group consisting of sickle cell trait; Hb-C, Hb-D, Hb-E, Hb-H, Hb-I, and Hb-Kansas disorders; or a combination of Hb-S with a second mutant β-globin allele.

11. The method of claim 1, wherein the therapeutic gas is administered in the absence of tobacco smoke.

12. The method of claim 1, wherein the therapeutic gas further comprises oxygen, the oxygen being in contact with the NO in the therapeutic gas for less than about 10 minutes prior to inhalation of the therapeutic gas by the patient.

13. The method of claim 12, wherein the therapeutic gas comprises at least 21% oxygen.

14. The method of claim 1, wherein the therapeutic gas further comprises gaseous carbon monoxide (CO) at a concentration of 1 to 10,000 ppm.

15. The method of claim 1, further comprising monitoring the concentration of NO in the therapeutic gas.

16. The method of claim 1, further comprising monitoring the concentration of $NO_2$ in the therapeutic gas.

17. The method of claim 1, wherein the therapeutic gas is exposed to an $NO_2$ scavenger prior to administering the therapeutic gas to the patient.

18. The method of claim 1, wherein the therapeutic gas comprises no more than 5 ppm $NO_2$.

19. The method of claim 1, further comprising measuring the hemoglobin $P_{50}$ of the patient both before and after the therapeutic gas is administered, wherein a decrease in the $P_{50}$, after the therapeutic gas is administered, relative to the $P_{50}$ before the therapeutic gas is administered, is an indication of the therapeutic effectiveness of the therapeutic gas.

20. The method of claim 7, further comprising determining the percent of sickled cells in the blood of the patient both before and after the therapeutic gas is administered, wherein a decrease in the percent of sickled cells after the gas is administered, relative to the percent of sickled cells before the gas is administered, is an indication of the therapeutic effectiveness of the therapeutic gas.

21. The method of claim 1, further comprising determining the level of Hb nitrosation after the therapeutic gas is administered.

22. The method of claim 1, wherein the concentration of NO in the therapeutic gas is 1 to 2,000 ppm, and the therapeutic gas is administered to the patient for at least one five-minute period per day for at least ten consecutive days.

23. A method for treating a patient identified as having a hemoglobinopathy, which method comprises identifying a patient having a hemoglobinopathy characterized by a reduced affinity of the patient's hemoglobin for oxygen compared with the affinity for oxygen of normal Hb-A; and administering to the patient a therapeutically effective amount of a NO-releasing compound.

24. The method of claim 23, wherein the NO-releasing compound is selected from the group consisting of S-nitrosothiols, NONOates, nitroprusside, nitrosoguanidine, glyceryl trinitrate, azide, and hydroxylamine.

25. The method of claim 23, wherein the NO-releasing compound is administered to the patient by a route selected from the group consisting of intravenous injection, intraarterial injection, transcutaneous delivery, oral delivery, and inhalation.

26. The method of claim 23, wherein the NO-releasing compound is administered by inhalation.

27. The method of claim 23, wherein the hemoglobinopathy is sickle cell disease.

28. The method of claim 27, wherein, prior to the administering step, the patient is diagnosed as suffering from sickle cell crisis.

29. A method of treating a patient identified as having a hemoglobinopathy, which method comprises identifying a patient having a hemoglobinopathy characterized by a reduced affinity of the patient's hemoglobin for oxygen compared with the affinity for oxygen of normal Hb-A; and contacting a portion of the patient's erythrocytes ex vivo or in situ with a therapeutically effective amount of NO.

30. The method of claim 29, wherein the hemoglobinopathy is sickle cell disease.

31. The method of claim 30, wherein, prior to the contacting step, the patient is diagnosed as suffering from sickle cell crisis.

32. The method of claim 29, wherein said NO is in gaseous form, and passes through a gas-permeable membrane prior to contacting said portion of the patient's erythrocytes.

33. A method of treating a patient identified as having a hemoglobinopathy, which method comprises identifying a patient having a hemoglobinopathy characterized by a reduced affinity of the patient's hemoglobin for oxygen compared with the affinity for oxygen of normal Hb-A; and administering a therapeutic gas to the patient, wherein the therapeutic gas comprises a therapeutically effective amount of gaseous CO.

34. The method of claim 33, wherein inhalation of the therapeutic gas by the patient produces 2–10% carboxy-Hb in the patient's blood.

35. The method of claim 33, wherein the CO has a concentration of 1 to 10,000 ppm in the therapeutic gas.

36. A method of decreasing the polymerization of sickle cell hemoglobin (Hb-S) in a patient, comprising identifying a patient the erythrocytes of which comprise Hb-S; and administering a therapeutic gas to the patient, wherein the therapeutic gas comprises an amount of gaseous NO sufficient to decrease the polymerization of Hb-S in the patient's erythrocytes.

37. The method of claim 36, wherein the therapeutic gas contains NO at a concentration of at least 1 ppm.

38. The method of claim 36, wherein the therapeutic gas contains NO at a concentration of at least 10 ppm.

39. The method of claim 36, wherein the therapeutic gas contains NO at a concentration of 40–2000 ppm.

40. The method of claim 36, wherein the therapeutic gas is administered to the patient for at least 10 seconds.

41. The method of claim 36, wherein the therapeutic gas is administered to the patient for at least 5 minutes.

42. The method of claim 36, wherein the therapeutic gas further comprises oxygen, the oxygen being in contact with the NO in the therapeutic gas for less than about 10 minutes prior to administration of the therapeutic gas to the patient.

43. The method of claim 36, wherein prior to administering the therapeutic gas, the patient is identified as being at risk of incurring a sickle cell crisis.

44. The method of claim 36, further comprising monitoring the concentration of NO in the therapeutic gas.

45. The method of claim 36, further comprising monitoring the concentration of $NO_2$ in the therapeutic gas.

46. The method of claim 36, wherein the therapeutic gas is exposed to an $NO_2$ scavenger prior to administering the therapeutic gas to the patient.

47. The method of claim 36, wherein the therapeutic gas comprises no more than 5 ppm $NO_2$.

48. The method of claim 36, wherein the concentration of NO in the therapeutic gas is 1 to 2,000 ppm, and the therapeutic gas is administered to the patient at least once per day for at least ten consecutive days.

49. The method of claim 36, wherein the therapeutic gas is administered to the patient while the patient undergoes surgery, or within one hour before or after surgery.

50. The method of claim 1, wherein the concentration of NO in the therapeutic gas is between about 10 and about 100 ppm.

51. The method of claim 1, wherein the concentration of NO in the therapeutic gas is between about 40 and about 100 ppm.

52. The method of claim 1, wherein the concentration of NO in the therapeutic gas is about 80 ppm in air, and the therapeutic gas is administered to the patient for at least one 45-minute period.

* * * * *